United States Patent
Konya et al.

(10) Patent No.: US 9,198,606 B2
(45) Date of Patent: Dec. 1, 2015

(54) TAPE MAGAZINE WITH REWIND LOCK AND INTEGRATED TAPE RELEASE

(75) Inventors: Ahmet Konya, Ludwigshafen (DE); Hans List, Hesseneck-Kailbach (DE); Hans-Jürgen Kuhr, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 220 days.

(21) Appl. No.: 13/479,006

(22) Filed: May 23, 2012

(65) Prior Publication Data

US 2012/0283528 A1  Nov. 8, 2012

(30) Foreign Application Priority Data

Nov. 24, 2009  (EP) ..................................... 09176917

(51) Int. Cl.
*A61B 5/155* (2006.01)
*A61B 5/02* (2006.01)
*A61B 5/145* (2006.01)
*A61B 5/15* (2006.01)

(52) U.S. Cl.
CPC ............ *A61B 5/1427* (2013.01); *A61B 5/02035* (2013.01); *A61B 5/14* (2013.01); *A61B 5/1405* (2013.01); *A61B 5/1411* (2013.01)

(58) Field of Classification Search
CPC ....................................................... A61B 5/155
USPC ......................................................... 600/583
See application file for complete search history.

(56) References Cited

U.S. PATENT DOCUMENTS

| 7,456,550 | B2 | 11/2008 | Deck |
| 7,883,473 | B2 | 2/2011 | LeVaughn et al. |
| 7,892,185 | B2 | 2/2011 | Freeman et al. |
| 8,202,232 | B2 * | 6/2012 | Konya et al. ................... 600/583 |
| 2005/0245954 | A1 * | 11/2005 | Roe et al. ....................... 606/181 |
| 2006/0052810 | A1 * | 3/2006 | Freeman et al. ............... 606/181 |
| 2006/0173380 | A1 | 8/2006 | Hoenes et al. |

(Continued)

FOREIGN PATENT DOCUMENTS

| CN | 1662174 A | 8/2005 |
| CN | 1822792 A | 8/2006 |

(Continued)

OTHER PUBLICATIONS

International Preliminary Report on Patentability, PCT/EP2010/067962, mailed Jul. 12, 2012.

*Primary Examiner* — Sam P Siefke

(74) *Attorney, Agent, or Firm* — Bose McKinney & Evans LLP

(57) ABSTRACT

A replaceable magazine for use in an analytic test instrument a plurality of analytic aids on a carrier tape. The analytic aids can be made available in an application position of the magazine by means of the carrier tape. The magazine has a supply reel for holding regions of the carrier tape with unused analytic aids and a take-up reel for holding regions of the carrier tape with used-up analytic aids. The carrier tape can be moved in a spooling direction from the supply reel to the take-up reel. The magazine has a rewind lock of the take-up reel. The magazine has a tape release device, which is configured to make available a take-up reel tape reserve of the carrier tape on the side of the application position facing the take-up reel. The take-up reel tape reserve enables a lifting movement of an analytic aid situated in the application position.

20 Claims, 5 Drawing Sheets

(56) References Cited

U.S. PATENT DOCUMENTS

| | | |
|---|---|---|
| 2006/0240403 A1* | 10/2006 | List et al. .................... 435/4 |
| 2009/0200413 A1 | 8/2009 | Sacherer |
| 2010/0049090 A1 | 2/2010 | Konya et al. |
| 2010/0198109 A1 | 8/2010 | Harttig |
| 2010/0216246 A1 | 8/2010 | Konya et al. |

FOREIGN PATENT DOCUMENTS

| | | |
|---|---|---|
| CN | 1833610 A | 9/2006 |
| CN | 101111189 A | 1/2008 |
| CN | 101506653 A | 8/2009 |
| DE | 28 03 345 B1 | 6/1979 |
| DE | 198 19 407 A1 | 11/1999 |
| EP | 1 690 496 A1 | 8/2006 |
| EP | 2 039 293 A1 | 3/2009 |
| JP | 2010-536516 | 12/2010 |
| WO | WO 03/071940 A1 | 9/2003 |
| WO | WO 03/088835 A2 | 10/2003 |
| WO | WO 2005/006985 A2 | 1/2005 |
| WO | WO 2006/059232 A1 | 6/2006 |
| WO | WO 2007/073912 A1 | 7/2007 |
| WO | WO 2008/022999 A1 | 2/2008 |
| WO | WO 2009/030359 A1 | 3/2009 |
| WO | WO 2009/039926 A1 | 4/2009 |

* cited by examiner

TAPE MAGAZINE WITH REWIND LOCK AND INTEGRATED TAPE RELEASE

RELATED APPLICATIONS

This application is a continuation of PCT/EP2010/067962, filed Nov. 23, 2010, which claims priority to EP 09 176 917.4, filed Nov. 24, 2009, both of which are incorporated herein by reference in their entirety.

BACKGROUND

The invention relates to a magazine for use in an analytic test instrument and to an analytic test instrument. Such analytic test instruments and magazines are used particularly in the field of medical diagnostics for generating and/or collecting and/or analyzing a sample of a body fluid. Analyzing the sample can in particular include a qualitative or quantitative analysis of the sample of the body fluid in respect of one or more analytes. By way of example, these analytes can be metabolites. Without restricting further possible fields of application, this analyte can, for example, be blood glucose, cholesterol, triglycerides, coagulates or the like.

The field of medical technology, in particular analytics, has disclosed a number of test instruments that require analytic aids. By way of example, there are known to be piercing instruments, in which a number of lancets can be used in succession, or analytic measurement instruments, in which a number of test elements can be made available in succession in order to detect at least one analyte in a sample of a body fluid.

In addition to test instruments that have drum magazines or similar supply devices for making available the analytic aids, tape instruments are finding increasing use of late; here, the analytic aids are made available by means of one or more carrier tapes. Thus, for example, German Patent No. DE 28 03 345 C2 describes a piercing device for obtaining blood; it comprises a tape magazine. In this case, individual lancets are lined up in succession on a tape. Similarly, German Patent No. DE 198 19 407 A1 describes a blood-glucose measurement instrument with a tape magazine for test strips. In February 2009, the Accu-Chek® Mobile test instrument from Roche Diagnostics GmbH became the first commercially available blood-glucose measurement instrument that makes use of a test strip tape cassette.

The advantage of the tape concept, whether for lancets or for test elements, generally lies in the relatively large number of analytic aids, e.g. test elements and/or piercing elements, that can be available in wound-up form in a comparatively small magazine. However, in general there is the problem here that a tape is relatively difficult to handle in practice compared to rigid carrier elements. Thus, in particular, tape instruments require a few additional technical measures in order to enable orderly guidance of the tape and, for example, prevent uncontrolled unwinding of the tape.

The prior art has disclosed so-called rewind locks for tape magazines, which can fix the carrier tape, particularly when the magazine is removed from the test instrument. This prevents already used-up test elements and/or piercing elements from reappearing so as to avoid the risk of unwanted contamination of the user and/or other parts of the analytic test instrument with a liquid sample or to prevent injury to the user.

Thus, for example, International Publication No. WO 2006/059232 A1 describes a measurement instrument with a test-sensor disk magazine. The disk magazine has a rewind lock which is only activated in the removed state of the magazine; by contrast, this lock is by-passed in the inserted state.

U.S. Publication No. 2009/0200413 describes a diagnostic test-strip tape cassette. It has a rotational safety device with locking teeth that should prevent inadvertent unwinding of test tape. This lock is active in the case of instrument-independent handling.

European Patent No. 1 690 496 B1 describes a blood-glucose measurement system with a test-strip tape magazine. A pawl ensures that a take-up reel, i.e. a holding reel for used-up tape sections of the test tape, can only rotate in one direction. This locking function is active in the inserted state of the magazine.

U.S. Pat. No. 7,883,473 also describes a piercing aid. It has a lancet magazine with an integrated rewind lock. This rewind lock should, in particular, prevent reuse of the lancets used at an earlier time.

International Publication No. WO 03/088835 A2 describes a system that is based on microsamplers stored on a tape magazine. This system is also provided with a rewind lock. A ratchet device ensures that tape transport can only take place in a forward direction. This is how the inserted tape magazine is secured against inadvertent rewinding.

U.S. Publication No. 2010/0216246 has disclosed a combination drive for a sample-obtaining system for obtaining a liquid sample. The sample-obtaining system has a coupling element for coupling to an analytic aid and a drive unit for driving a movement of the coupling element. The drive unit furthermore has a coupling device with at least one rotational-direction sensitive element, with the coupling device being configured to couple an energy transducer to a first system function in a first rotational direction and to a second system function in a second rotational direction.

However, in practice there are a few technical challenges in known test instruments that are based on the use of a tape magazine. In particular, there are test instruments in which a lifting movement is carried out in at least one application position with an analytic aid situated there. By way of example, this lifting movement can be a rapidly carried out piercing movement and/or a slowly carried out sample-taking movement. Thus, for example, a lancet can be used to perforate a skin section of a user and/or a liquid sample of the body fluid can be collected using a test element in the application position. However, a problem in the case of such lifting movements of analytic aids stored on a tape magazine lies in a release of the tape. By way of example, a taught carrier tape only has limited suitability for a piercing or blood-collecting procedure. Releasing the tape enables a deflection of the carrier tape during the lifting movement in which the carrier tape is also moved and as a result avoids overstretching, a lasting deformation or even a tearing of the carrier tape.

U.S. Publication No. 2010/0049090 describes a piercing system with a lancet carrier tape that carries a plurality of lancets. In a piercing movement, the piercing drive moves a lancet brought into the piercing position together with a section of the lancet carrier tape carrying this lancet in the piercing direction. After a lancet was brought into the piercing position, at least one part of a transport apparatus, arranged behind the piercing position in the conveying direction, carries out a movement before or during the piercing movement of said lancet. It is furthermore proposed that a winding apparatus on the inserted cassette carries out a rewinding step in order to unwind carrier tape from the take-up reel for the respective piercing movement.

Hence, in general it should be noted that lancets, test elements or microsamplers stored in a magazine generally require a rewind lock in order to provide the user with the necessary hygiene and safety when handling the medical product. These rewind locks can, in principle, be applied to analytic aids stored in a tape magazine. However, a disadvantage of the known systems is the fact that the presence of a rewind lock is often contradictory to the requirement of a tape release, i.e. reversed tape unwinding during the lifting movement, for example during the piercing or sample-collecting process. However, the tape release in many cases requires rewinding of carrier tape already wound onto the take-up reel because otherwise there would be uneven load on an actuation system of the test systems, e.g. a lancet gripper. By way of example, the consequence of this would be oblique piercing, slipping of the lancet in the gripper, blocking of the piercing actuation system or the like.

Releasing the tape is required in many cases in order to provide deflecting carrier tape to be deflected during the piercing process with enough play. However, for this, most solutions known from the prior art do not provide an answer to the presence of a rewind lock. An active rewinding movement of the take-up reel drive does not suffice in many cases if the rewind lock of the magazine does not support this function or offers other alternatives for releasing the tape.

Particularly in the case of test instruments and tape magazines comprising a permanently acting, integrated rewind lock, it is thus possible to establish that there is a conflict of goals with a lifting movement of a test element. Here, an integrated rewind lock should in general be understood to mean a rewind lock that is integrated into the magazine and thus is able to prevent rewinding without requiring a drive of the test instrument. On the one hand, such an integrated rewind lock is often desirable since it prevents inadvertent unwinding of carrier tape from the take-up reel, even if the magazine is separated from the test instrument; on the other hand, it is however precisely lifting movements that require even unwinding of carrier tape from the supply reel and from the take-up reel in order, for example, to enable a tension-free lifting movement of the test element.

The solutions known from the prior art, such as, for example, the one in International Publication No. WO 2006/059232 A1, in which a rewind lock is by-passed when the magazine is inserted into the test instrument, are, in part, technically very complex. Such releases would furthermore generally lead to released tape material being fixed loosely after the piercing and possibly falling out of a tape guide. A correspondingly complex control of the take-up reel drive could compensate for these circumstances.

SUMMARY

The present invention provides a magazine and an analytic test instrument which at least largely avoid the disadvantages of known magazines and analytic test instruments. In particular, the above-described conflict of goals between a rewind lock and a tape release can be resolved in a technically simple fashion using these teachings.

In a first aspect of this disclosure, a magazine for use in an analytic test instrument is proposed. Here, a magazine should be understood to mean a device that can hold and make available a plurality of analytic aids. The magazine can, as will be explained in more detail below, more particularly be embodied as a tape magazine, for example as a tape cassette, and can in general have a magazine housing, for example.

In general, an analytic test instrument should be understood to mean an instrument that is able to carry out at least one medical function, more particularly an analytic and/or diagnostic function. In particular, the analytic test instrument can carry out one or more of the following functions: generating a sample of a body fluid, more particularly by perforating a skin section of a user; detecting at least one analyte in a sample from a body fluid, more particularly detecting glucose and/or cholesterol and/or triglycerides and/or detecting coagulation; collecting a sample of a body fluid, more particularly by a capillary action.

The magazine is embodied as a replaceable magazine. This means that a user can remove the magazine from the analytic test instrument in order to insert a new, unused magazine into the analytic test instrument. By way of example, the analytic test instrument may have a receptacle for this purpose, into which, for example after opening a housing of the test instrument, the magazine can be inserted or plugged. Hence, the magazine is not permanently connected to the analytic test instrument. By way of example, the magazine itself may not have its own actuation system, or only have an incomplete actuation system, such that the aforementioned medical function can only be carried out in conjunction with the analytic test instrument, which may comprise such an actuation system. Furthermore, a magazine housing of the magazine can, for example, have corresponding guides, grooves, fixing elements or positioning aids in order to enable a reversible insertion of the magazine into the analytic test instrument and/or a reversible attachment of the magazine onto the analytic test instrument.

The magazine has a plurality of analytic aids on a carrier tape. Here, an analytic aid should be understood to mean an aid that can be used for at least one medical function of the analytic test instrument. In particular, this may be a sample-generation function and/or a sample-collection function and/or an analysis function. Accordingly, the analytic aids may comprise one or more of the following analytic aids: a lancet, i.e. any element for piercing and/or cutting through or generally perforating a skin section of a user; an element for holding and transporting a sample of a body fluid from the user, more particularly a capillary and/or a capillary gap; a test element with at least one test chemical for detecting at least one analyte in the body fluid. By way of example, the test chemical can be a material that changes at least one physically and/or chemically detectable property in the presence of the at least one analyte to be detected. Such test chemicals are known from the prior art. By way of example, the test element can be an electrochemical and/or an optical test element. By way of example, the test element can comprise at least one test field. Here, the analytic magazine can be embodied such that it merely makes available one type of analytic aid. Alternatively, it is also possible that a number of types of analytic aids are made available, for example on an alternating basis. It is also possible that there are integrated analytic aids, which unify a number of the aforementioned functions. Thus, for example, microsamplers are known, which contain a lancet function and a capillary function and can likewise be used as an analytic aid within the scope of this disclosure. Integrated lancets with test elements are also possible, optionally with an additional capillary, for example.

In general, a carrier tape is understood to mean a continuous support, by means of which analytic aids can be made available in succession. Thus, in addition to a simple tape, for example a paper tape, a tape made of plastic, a multilayered laminate tape or similar tapes, other types of continuous supports are also possible, for example link chains or the like. By way of example, the analytic aids can be arranged on the carrier tape and/or be integrated into the carrier tape and/or be connected to the carrier tape in a different manner. By way of example, the analytic aids can be arranged on the carrier tape at equidistant intervals. Thus, for example, lancets can be arranged on the carrier tape and/or test elements can be arranged on the carrier tape, for example in the form of test fields.

The carrier tape can be used to make the analytic aids available in at least one application position of the magazine. Here, an application position should be understood to mean a position in which at least one function of the analytic test instrument interacts with the analytic aid, the latter being situated in said application position. By way of example, this application position can be a position in which a lancet carries out a piercing movement and/or a sample-collection movement. Alternatively, or in addition thereto, the application position can also be a position in which a sample-taking movement is carried out. By way of example, an actuation system of the analytic test instrument can be provided for carrying out this function, as will be explained in more detail below.

By way of example, the analytic magazine and the analytic test instrument can be embodied such that the carrier tape is used to make the analytic aids successively available in the at least one application position. It is also possible for a plurality of application positions to be provided, for example an application position for taking a sample and an application position for evaluating the sample. By way of example, the carrier tape can be wound on such that a new, still unused analytic aid can respectively be made available in the application position of the magazine.

The magazine furthermore has at least one supply reel for holding regions of the carrier tape with unused analytic aids, and also at least one take-up reel for holding regions of the carrier tape with used-up analytic aids. Hence, the analytic test instrument can be configured to drive the take-up reel and/or the supply reel by means of a transport mechanism such that the carrier tape is respectively wound on such that a new, unused analytic aid is made available in the application position. Thus, the analytic test instrument preferably comprises a drive, which can drive the take-up reel, in particular, to a rotational movement, more particularly to a cycled rotational movement. This onward transport of the carrier tape is, in general, also referred to as "spooling" below. The carrier tape can be moved in a spooling direction from the supply reel to the take-up reel.

The magazine furthermore has a rewind lock of the take-up reel. This rewind lock, which can be wholly or partly integrated into the magazine, should be understood to mean an apparatus that prevents rewinding of the take-up reel, i.e. a movement of the carrier tape counter to the spooling direction at least to the extent where an already used-up, i.e. used, analytic aid once again reaches the application position. Thus, the rewind lock need not necessarily be embodied such that it prevents complete rewinding of the take-up reel, but rather it may permit minor rewinding or even encourage this, as will be explained in more detail below. However, this rewinding should not be made possible to the extent that already used analytic aids once again reach the application position. Alternatively, the rewind lock can also be embodied such that it prevents complete rewinding.

As will be explained in more detail below, the fact that the rewind lock is part of the magazine constitutes an advantage of the magazine because an integration of a rewind lock into the magazine leads to affording the possibility of reliably precluding rewinding of already used analytic aids in the used and removed magazine, for example of a used tape cassette, and also undesired and uncontrolled unwinding from the tape.

The magazine furthermore has a tape release device, which is configured to make available a take-up reel tape reserve of the carrier tape on the side of the application position facing the take-up reel. Hence, a side of the application position facing the take-up reel should be understood to mean part of the carrier tape that has already passed the application position in the spooling direction and hence moves toward the take-up reel or is already wound-up on the take-up reel.

In particular, the take-up reel tape reserve can enable a lifting movement of an analytic aid situated in the application position, either on its own or by interacting with a tape reserve on the side of the application position facing the supply reel. Hence, in general, a tape reserve should be understood to mean a tape section that makes possible the lifting movement of the analytic aid, including the part of the carrier tape connected to this analytic aid, without significant tension being exerted on the carrier tape, which could lead to a deformation of the carrier tape or even to the latter tearing. Hence, a tape reserve is a tape section that can make available the additionally required carrier tape for the lifting movement. Here, the tape reserve on the take-up-reel side of the application position is generally referred to as take-up reel tape reserve, and supply reel tape reserve refers to the optional additional tape reserve of the supply-reel side of the application position.

Accordingly, the magazine can more particularly be embodied such that a supply reel tape reserve of the carrier tape can additionally be made available on the side of the application position facing the supply reel, which can include the supply reel itself. The magazine is typically configured such that the supply reel tape reserve substantially corresponds to the take-up reel tape reserve. Here, "substantially" is typically understood to mean complete correspondence of these tape reserves z; however, within the scope of this term, it is also possible to tolerate a deviation of no more than 30%, more particularly of no more than 20% and particularly preferably of no more than 10%.

Thus, for example, the magazine can be configured such that the complete tape reserve, which can be composed of the take-up reel tape reserve and, optionally, the supply reel tape reserve, has a symmetric embodiment and is composed of these two tape reserves in equal measure. As a result, it is possible that, for example, an actuator and/or a gripper are loaded uniformly. By way of example, this makes it possible, at least in part, to prevent jamming and/or an oblique lifting movement, for example oblique piercing.

On the side of the application position facing the supply reel, it is possible for the supply reel itself to make available the supply reel tape reserve since the supply reel can in any case allow a tape release because, during such a tape release, the supply reel is rotated in its usual rotational direction, which occurs during onward cycling.

Here, in general, a lifting movement should be understood to mean the movement of the analytic aid in the application position, which occurs during the correct use of the analytic aid in the analytic test instrument. By way of example, the analytic aid may be fixed during a lifting movement, for example by means of at least one gripper in the application position. By way of example, the lifting movement can be a piercing movement and/or a sample-taking movement. By way of example, a lancet can be used for a lifting movement in the form of a piercing movement by means of a gripper of the analytic test instrument. Such a lifting movement then comprises a rapid forward movement, for example with a top speed of 2 to 5 m/s, during which the skin section is perforated, followed by a backward movement. It is also possible for a sample to be taken during the backward movement, for example by means of a capillary gap. Alternatively, the lifting movement in the form of the sample-taking movement may contain a forward movement of a test field up to a wound and/or a sample on a skin surface of the user, during which the test field or test element is briefly brought into contact with the liquid sample such that liquid sample is applied to the test field. By way of example, this sample-taking movement can be slow, for example with a top speed of less than 1 m/s, for example with a speed of 0.01 to 0.5 m/s. By way of example, a gripper and/or another type of actuator as well can also be used for this.

In general, the lifting movement of an analytic aid situated in the application position may, for example, have a maximum lift, which may be fixedly prescribed or which may also be embodied in an adjustable fashion. In particular, the take-up reel tape reserve can be 0.2 to 0.8 of the maximum lift, preferably 0.5 of the maximum lift. However, the take-up reel tape reserve can in principle assume all values between zero and the maximum lift, depending on the design of the reels. In general, this only depends on the type of tape guidance relative to the lifting direction and can, for example, be illustrated by considering limit values. By way of example, if the carrier tape runs perpendicular to the lifting direction, the lifting movement generally plays almost no role. The required take-up reel tape reserve can virtually be taken from the displacement of the tape. However, if the tape runs substantially parallel to the lifting movement, each reel side must, in general, provide a complete lifting length as tape reserve. The value of 0.5 of the maximum lift, set forth above, therefore constitutes a mean value that is often found in practice. By way of example, the maximum lift can be 0.5 to 10 mm, more particularly 1 to 8 mm and preferably 3 to 6 mm.

The tape release device can furthermore be configured to hold once again, completely or at least in part, the take-up reel tape reserve after the lifting movement of the analytic aid. To this end, the tape release device can for example comprise a tape reservoir, from which the take-up reel tape reserve for the lifting movement can be taken and to which the take-up reel tape reserve can be resupplied after the lifting movement. By way of example, as will be explained in more detail below, this tape reservoir can be embodied in the form of at least one moveably mounted deflection element. However, other types of tape reservoirs are also possible, more particularly tape reservoirs that can fashion a variable length of the part of the carrier tape held between the application position and the take-up reel in order to be able to make available the take-up reel tape reserve. However, as an alternative or in addition thereto, the tape release device can also be wholly or partly integrated into the take-up reel; this will be explained in more detail below. The embodiment of the tape release device in which the latter is furthermore configured to once again hold the take-up reel tape reserve after the lifting movement of the analytic aid can furthermore also prevent entangling of the tape as a result of excessive tape after the lifting movement, which could lead to jamming, catching, slipping or entangling of the carrier tape.

The tape release device (tape release) is typically only provided on the take-up-reel side of the application position, i.e. on the side facing the take-up reel as seen from the application position. On the side facing the supply reel, between the application position and the supply reel, usually no such tape release device is provided. Here, the supply reel acts as tape release itself and provides the required supply reel tape reserve if a sufficient amount of tension is exerted on the carrier tape, for example during tape transport and/or during the lifting movement, such that an additional tape release device can be dispensed with on the side of the application position facing the supply reel. In other words, the supply reel alone can act as tape release device on the supply-reel side of the application position, with a tape release device being provided on the take-up-reel side, which can, more particularly, be arranged between the application position and the take-up reel and/or in the take-up reel itself. Compared to known tape guides, this embodiment is advantageous in that it is possible to dispense with an additional tape release device, which generally is without a technical effect in any case, on the supply-reel side, which can serve for technical simplification, a reduction in the production costs and a reduction in the installation space. Moreover, this allows the tape always to be held under sufficient tension, and it is possible to avoid an undesired release of tape by an additional tape release device between the application position and the supply reel, which could lead up to uncontrolled unwinding of tape on the supply-reel side.

In particular, the magazine can be embodied such that an analytic aid, which is situated in the application position, can be fixed by means of at least one fixing device, more particularly at least one gripper. The fixing device may, as a whole or in part, be a component of the magazine, but it can also be wholly or partly contained in an analytic test instrument that uses and/or comprises the magazine.

In the preferred case in particular, in which no tape release device is provided between the application position and the supply reel on the supply-reel side of the application position facing the supply reel and in which at least one tape release device is provided merely on the take-up-reel side of the application position, for example between the application position and the take-up reel and/or in the take-up reel, but in principle in other cases as well, it is particularly preferred if the analytic aid, respectively provided for use, is or can be fixed in the transport direction in the application position. By way of example, this can be brought about by a gripper, for example the gripper mentioned above, and/or by another fixing device, which may be configured to briefly fix an analytic aid situated in the application position such that it is impeded from further movement in the transport direction. By way of example, this fixing may take place for the period of time required for taking a sample and/or for a lancet movement, and optionally for a predetermined period of time before and/or after this movement. There can subsequently be a release, for example by reopening a gripper and/or another type of fixing device such that onward transport is made possible. By way of example, such fixing can be brought about by an interaction with a drive of the analytic aid, for example a lancet drive for carrying out a lancet movement and/or a drive for a test element for carrying out a sample-taking movement, with, for example, it being possible that the drive comprises the above-described gripper and/or the above-described fixing device.

In the case of a deflection movement of the tape without fixing the analytic aid, the required tape release could generally originate in a one-sided manner from the supply reel because this supply reel generally has a lower retention force, for example as a result of a freewheel. As a consequence, an uneven force distribution would arise on the analytic aid and this could deflect the aid at an angle. Moreover, the forced tape release would possibly not be wound up by the take-up-reel side tape release device since the latter generally does not automatically also turn in during the deflection process. Hence, this would, at least briefly, result in loose tape, which could only be removed by the subsequent winding process of the take-up reel. However, this is permanently associated with the risk that the tape slips its guide after the deflection and hence becomes unusable. Hence a symmetric tape release can generally only be achieved by fixing the analytic aid during the deflection.

As explained above, the rewind lock is configured such that it at least largely prevents rewinding of the take-up reel during which a relatively large amount of carrier tape with already used-up analytic aids would carry out a movement counter to the spooling direction. However, rewinding by small paths counter to the spooling direction, for example by a path that is less or significantly less than the spacing between the analytic aids on the carrier tape, for example less than 0.8 of this spacing, more particularly less than 0.5 of this spacing and preferably less than 0.3 or even 0.2 of this spacing, may be made possible and may even be desirable for the purpose of releasing the tape, as will be explained in more detail below.

The rewind lock is typically a permanently acting rewind lock, i.e. a rewind lock that is effective both when the magazine is situated outside of the analytic test instrument and also when the magazine has been inserted into the analytic test instrument. In particular, this means that the rewind lock is typically not configured to be by-passed when the magazine is inserted into the analytic test instrument.

In particular, the rewind lock can comprise one or more of the rewind locks described in the following text. Thus, in particular, the rewind lock can comprise at least one rotational-direction sensitive element. More particularly, in this case it can comprise a rotational-direction sensitive element connected to the take-up reel. Here, a rotational-direction sensitive element should be understood to mean an element that enables a rotation in one direction and at least largely prevents a rotation in another direction. Here, at least largely preventing should be understood to mean prevention that is preferably complete, but which may also comprise small rewinding, for example through a dead angle through which rewinding still is possible. Such a dead angle can even be used in a targeted manner in order to make available the take-up reel tape reserve; this will be explained in more detail below.

Alternatively, or in addition thereto, the rewind lock can have at least one freewheel, more particularly at least one freewheel connected to the take-up reel. Here, a freewheel should generally be understood to mean a device that, in a drive with a drivetrain, decouples part of the drivetrain from a rotational movement if load conditions change. In particular, the freewheel can be a particular embodiment of a rotational-direction sensitive element. Various embodiments of a freewheel are known from the prior art, and said freewheel may for example comprise a pawl freewheel, a wrap spring, a clamping body and/or clamping roller freewheel or other types of freewheel.

Alternatively, or in addition thereto, the rewind lock can also comprise at least one ratchet. A ratchet should likewise be understood to mean an element with one or more pawls, which can engage in corresponding counterparts such that movement is made possible in one direction but movement in another direction is prevented. The ratchet can more particularly be connected to a take-up reel. The above-described freewheel can for example be a special case of such a ratchet or be embodied as a ratchet. In general, the rotational-direction sensitive element can more particularly comprise at least one pawl, more particularly a pawl connected to the take-up reel and/or a pawl connected to a magazine housing. It is also possible to provide a design with a plurality of pawls. The pawls can enable a linear drive or else a rotational drive in one direction and prevent it in another direction.

As another alternative or in addition thereto, the rewind lock can also contain at least one rewind lock acting on the carrier tape. Thus, for example, the rewind lock may comprise a rotational-direction-dependent brake acting on the carrier tape. Such a rotational-direction-dependent brake brakes the carrier tape in the case of movement counter to the spooling direction and by contrast allows movement in the spooling direction. There may be immediate onset of braking in the case of movement counter to the spooling direction, or only after a design-dependent or predetermined braking path. Here, the effect can be exerted directly on the carrier tape, or indirectly, for example by not directly braking the carrier tape but rather by braking one or more analytic aids connected to said carrier tape.

In particular, a rotational-direction-dependent brake can be implemented by means of at least one roller. By way of example, use can be made of a roller gap between a roller and a counter element, for example a second roller. By way of example, the at least one roller and/or the at least one double roller can be embodied such that these have a deformable roller material. While a movement through the roller gap is made possible in the spooling direction, the roller locks in the case of movement counter to the spooling direction, resulting in a deformation of the roller material, as a result of which the roller gap is narrowed and the carrier tape is braked. More particularly, this at least one roller can thus be a rubber roller.

As another alternative or in addition thereto, use can also be made of at least one spring-loaded element acting on the carrier tape. By way of example, a spring-loaded flap can act on the carrier tape and/or on one or more of the analytic aids connected to the carrier tape. By way of example, the spring-loaded element can lie on the carrier tape at an angle such that analytic aids can pass the spring-loaded element in the spooling direction; by contrast, the analytic aids can be caught on the spring-loaded element counter to the spooling direction and cause a braking of the carrier tape. Thus, in particular, the spring-loaded element can be embodied as an asymmetric spring-loaded element, which lies on the carrier tape and allows passage of the carrier tape and/or the analytic aids in the spooling direction, but prevents or at least brakes passage of the analytic aids counter to the spooling direction. Here, the spring-loaded element may have a rigid embodiment, or else be deformable, with, in the latter case, a deformation for example being able to occur when the carrier tape and/or the analytic aids move counter to the spooling direction. Here, the deformation can ensure a braking effect as a result of increased forces acting on the carrier tape and/or the analytic aids. Here, a spring load can be understood to mean a load on the element by a separate spring or else, alternatively or in addition thereto, an element that itself at least in part has elastic properties such that the element itself can exert the spring effect. In particular, the spring-loaded element can comprise at least one spring-loaded flap.

As another alternative or in addition thereto, the rewind lock can also comprise at least one sealing lip acting on the carrier tape. A sealing lip can also be embodied as a special case of the above-described spring-loaded element, and so a sealing lip can, for example, have two spring-loaded elements that act on the carrier tape and/or the analytic aids from opposite sides. Here, a sealing lip should be understood to mean an element that is able to provide a gap through which the carrier tape with the analytic aids is routed. Here, lips that are deformable or that can change in terms of their position act on the carrier tape and/or the analytic aids from both sides of the gap. The lips can also, at least in sections, have deformable properties, for example plastic and/or elastic properties. In respect of the effect of such deformable properties, reference can be made to the description above in relation to the effect of deformable spring-loaded elements. The effect of the sealing lip should once again be such that the carrier tape and/or the analytic aid are allowed to pass the sealing lip in the spooling direction of the carrier tape; however, passage through the sealing gap counter to the spooling direction is prevented or at least braked. By way of example, a braking effect can once again occur when analytic aids impact on the sealing lip. Alternatively, or in addition thereto, the braking effect can be implemented such that the sealing lip is deformed if the carrier tape passes through the gap in the sealing lip against the spooling direction such that the gap is made narrower, and so a force or an increased force acts on the carrier tape and/or the analytic aids.

The analytic magazine can furthermore optionally have at least one brake. This brake can be configured to brake rewinding of the take-up reel and/or winding-on of the supply reel. In respect of possible embodiments of this optional brake, reference can for example be made to U.S. Publication No. 2006/0240403 A1. However, other embodiments are also possible. Although this is possible, the brake particularly need not act directly on the carrier tape but rather may act on the supply reel and/or on the take-up reel and/or an element that is co-rotating with the supply reel and/or the take-up reel.

The tape release device can be embodied in different ways in order to implement the functionality described above. Thus, for example, the tape release device can at least partly be integrated into the rewind lock and/or at least partly be embodied as a separate element embodied separately from the rewind lock. A mixture of these options is also feasible, i.e. a form in which the tape release device is partly integrated into the rewind lock and partly embodied separately and independently of the rewind lock.

In a first embodiment, the tape release device (tape release) can be partly or completely integrated into the rewind lock. This means that the tape release device and the rewind lock can at least in part be embodied with identical components.

In particular, this can be implemented such that a function of the rewind lock is dependent on a position of the carrier tape. By way of example, the locking or at least braking function of the rewind lock in the case of movement of the carrier tape counter to the spooling direction may depend on how the absolute position of the carrier tape, the absolute position of analytic aids, the relative position of the carrier tape relative to the rewind lock, the relative position of the analytic aids and/or a specific analytic aid relative to the rewind lock, a rotational angle of the take-up reel or a rotational angle of the supply reel are currently set. Thus, for example, a position of the carrier tape can comprise an absolute position, a relative position, a rotational angle of the supply reel or a rotational angle of the take-up reel.

The rewind lock can accordingly be configured to largely prevent, or at least brake, a movement of the carrier tape counter to the spooling direction in a plurality of locking positions, with a movement of the carrier tape counter to the spooling direction being at least largely made possible between the locking positions until a next locking position is reached, the take-up reel tape reserve, or at least part of the take-up reel tape reserve, being released when the carrier tape moves counter to the spooling direction.

This plurality of locking positions, which can also comprise more stretched-out locking regions, can be implemented in a number of different ways. Thus, for example, the rewind lock can comprise at least one rotational-direction sensitive element, more particularly a rotational-direction sensitive element connected to the take-up reel. This should enable a rotation in one direction and at least largely prevent a rotation in another direction. In respect of possible embodiments of the rotational-direction sensitive element, reference can be made to the description above. Here, "at least largely prevent" can for example also include the provision of a dead angle, through which rewinding in a locking direction is still possible. Thus, the rotational-direction sensitive element can have a dead angle and enable rewinding through this dead angle, the magazine being configured to release the take-up reel tape reserve during rewinding.

Alternatively, or in addition thereto, the rewind lock can have at least one spring-loaded element acting on the carrier element, more particularly a spring-loaded flap, and/or at least one sealing lip. Accordingly, reference can be made to the description above in respect of the possible embodiments of such elements. The analytic aids can pass the spring-loaded element when the carrier tape moves in the spooling direction, whereas these analytic aids and/or the carrier tape can jam against or at least be braked at the aforementioned elements when the carrier tape moves counter to the spooling direction. Hence locking positions can respectively be the positions of the carrier tape in which respectively one analytic aid impacts on the spring-loaded element acting on the carrier tape and/or the sealing lip during movement counter to the spooling direction. By contrast, if the analytic aid is situated in another position, rewinding counter to the spooling direction is possible in each case by a length of the carrier tape until the next analytic aid impacts on the spring-loaded element. This length of tape can be used as take-up reel tape reserve.

Likewise, as another alternative or in addition thereto, the rewind lock can have at least one roller, more particularly at least one double roller. The carrier tape can be routed through a gap delimited by the roller. As already described above, the roller can undergo a deformation when the carrier tape moves counter to the spooling direction, with the deformation leading to a narrowing of the gap and further movement of the carrier tape at least being impeded. In this case, the rewind lock and the tape release device also at least in part have identical components.

The tape release can also be designed to be at least partly independent of the rewind lock. This means that the tape release is embodied at least not to have wholly identical components with the rewind lock and is typically embodied entirely as a separate element. This too can be implemented in a number of ways.

Thus, the tape release can for example have a moveably mounted tape deflection. Such a moveably mounted tape deflection can for example be a so-called "dancer" or comprise such a dancer, which has a deflection roller connected to the carrier tape, said deflection roller being moveably mounted and pushed against the carrier tape with force by means of at least one spring element. The moveably mounted tape deflection can more particularly be provided between the application position and the take-up reel. The tape deflection can more particularly have at least one moveably mounted and spring-loaded roller, more particularly a "dancer" as defined above.

The moveably mounted tape deflection can more particularly be configured to be able to assume at least three positions. In particular, provision can be made here for a rest position with a maximum deflection of the moveably mounted tape deflection, i.e. a maximum deflection of the carrier tape. Furthermore, provision can be made for a tape transport position with a medium deflection. Here, a medium deflection should not necessarily be understood to mean a geometric and/or arithmetic mean, but rather any position between a maximum and a minimum deflection. By way of example, this tape transport position can be assumed by the moveably mounted tape deflection during an onward cycling of the magazine, more particularly during spooling of the carrier tape in the spooling direction. Furthermore, provision can be made for a lift position, i.e. a position which can be assumed by the moveably mounted tape deflection during the lifting movement and has a minimal deflection. In addition to these positions, further positions may be available and may be assumed.

In a further aspect, an analytic test instrument is proposed, which has at least one magazine as per one or more of the above-described embodiments. The analytic test instrument is configured to enable a replacement of the magazine. The analytic test instrument furthermore has a drive for driving the carrier tape, more particularly the take-up reel. The analytic test instrument is furthermore configured to carry out a lifting movement by means of an analytic aid situated in the application position. By way of example, the analytic test instrument may have at least one actuator for this purpose, which, together with the analytic aid situated in the application position, carries out the lifting movement, more particularly a piercing movement and/or a sample-taking movement. By way of example, this actuator can comprise at least one gripper for gripping the analytic aid and/or a tappet, by means of which the lifting movement can be carried out.

The release of the take-up reel tape reserve by the tape release device can in particular be controlled by the analytic test instrument. Thus, the analytic test instrument can for example have at least one sensor for identifying the position of the carrier tape. This can, as described above, for example be an absolute position of the carrier tape (for example an absolute position of at least one position marker of the carrier tape) and/or a relative position, for example a relative position assumed by a specific analytic aid, or by a number of analytic aids, relative to a measurement point. By way of example, such a sensor can be embodied such that incidence of an analytic aid at a specific measurement position is detected in an optical, electric, mechanical or acoustic manner. However, other types of detection are also possible. Accordingly, the at least one sensor can have corresponding sensor elements for identifying this incidence. The analytic test instrument can accordingly furthermore have a control which is configured to set the take-up reel tape reserve in accordance with the identified position of the carrier tape. By way of example, this control can comprise at least one electronic element, more particularly at least one data processing device. However, simpler controls are also possible, for example simple electronic triggers that enable a release. "Setting" the take-up reel tape reserve can for example be understood to mean that there is onward spooling of the carrier tape after identifying that a specific measurement position of the analytic aid has been reached, for example onward spooling by a predetermined amount.

By way of example, this can be combined with the above description relating to the embodiment of the magazine, in which a plurality of locking positions are provided. In particular, as described above, the magazine can thus be configured such that a function of the rewind lock is dependent on a position of the carrier tape, the rewind lock being configured to prevent a movement of the carrier tape counter to the spooling direction in a plurality of locking positions, whereas a movement of the carrier tape counter to the spooling direction is made possible between the locking positions until a next locking position is reached. The take-up reel tape reserve can then be released when the carrier tape moves counter to the spooling direction. If such an embodiment of the magazine is provided, the control can be configured to enable, more particularly to initiate, onward transport of the carrier tape equal to the take-up reel tape reserve, or by a value which at least approximately corresponds to the take-up reel tape reserve, when a predetermined locking position is reached. This makes it possible to implement the carrier tape being transported beyond the locking position by precisely the take-up reel tape reserve such that rewinding is enabled until the locking position is reached once again, as a result of which the take-up reel tape reserve is made available.

The disclosed embodiment of the magazine and the analytic test instrument has a number of advantages compared to known magazines and analytic test instruments. These advantages emerge in particular if the rewind lock in the magazine should not be mechanically by-passed when the magazine has been inserted into the analytic test instrument in order to implement the tape release. By means of the concepts proposed above, it is possible to make available at least a small take-up reel tape reserve in the magazine, for example in a magazine housing. By way of example, as explained above, this take-up reel tape reserve can correspond to approximately half of the maximum lift of the lifting movement, for example carried out by the tape during a piercing process and/or another type of lifting movement.

The optional supply reel tape reserve can, for reasons of symmetry, more particularly be taken from the supply reel so that, for example, a lancet gripper is loaded as evenly as possible. Thus, the whole tape release can be subdivided into the tape reserve on the take-up-reel side as seen from the application position, which is sketched out above and provided by means of the tape release device, and a tape reserve on the supply-reel side:

overall tape release=take-up reel tape reserve+supply reel tape reserve≈2·take-up reel tape reserve.

A typical lifting movement is in the region of between 3 mm and 6 mm, which therefore also approximately corresponds to the required tape release. A preferred take-up reel tape reserve, which is provided on the take-up-reel side by the tape release device sketched out above, thus preferably lies between 1.5 and 3 mm.

The supply reel tape reserve on the supply-reel side is easy to implement technically since the supply reel generally has a freewheel and generally automatically releases carrier tape with unused analytic aids if a minimum tension $F_{min}$ is exceeded. This principle is already used during normal tape transport, with the drive of the take-up reel generally providing this tension $F_{min}$. In the case of a piercing process, the minimum tension must be achieved by a corresponding actuator in order to unwind the supply reel tape reserve on the supply-reel side from the supply reel. By way of example, this actuator can comprise a gripper mechanism and/or a piercing drive. By contrast, on the side of the take-up reel, the situation is less expedient in the case of magazines according to the prior art, as explained above. In general, the drive of the take-up reel is normally inactive and therefore blocks rewinding of the take-up reel as a result of the rewind lock. However, by using the solution according to this disclosure, as described above, by means of which it is possible to make available a take-up reel tape reserve despite an integrated rewind lock, it is easy to solve this problem, and hence the conflict of goals presented at the outset, without much technical complexity.

Hence it is possible to implement an in particular permanent integrated rewind lock in a magazine, more particularly in a tape magazine. This rewind lock can prevent a user inadvertently unwinding tensioned material from the take-up reel, for example after the removal of the magazine from the analytic test instrument. Hence the rewind lock can be active at all times.

BRIEF DESCRIPTION OF THE DRAWINGS

Further features and details of the disclosed embodiments emerge from the following description. The exemplary embodiments have been illustrated schematically in the figures. Here, the same reference signs denote equivalent or functionally equivalent elements, or elements that correspond to one another in respect of their functions. The invention is not restricted to the exemplary embodiments.

DETAILED DESCRIPTION

Figure 1:
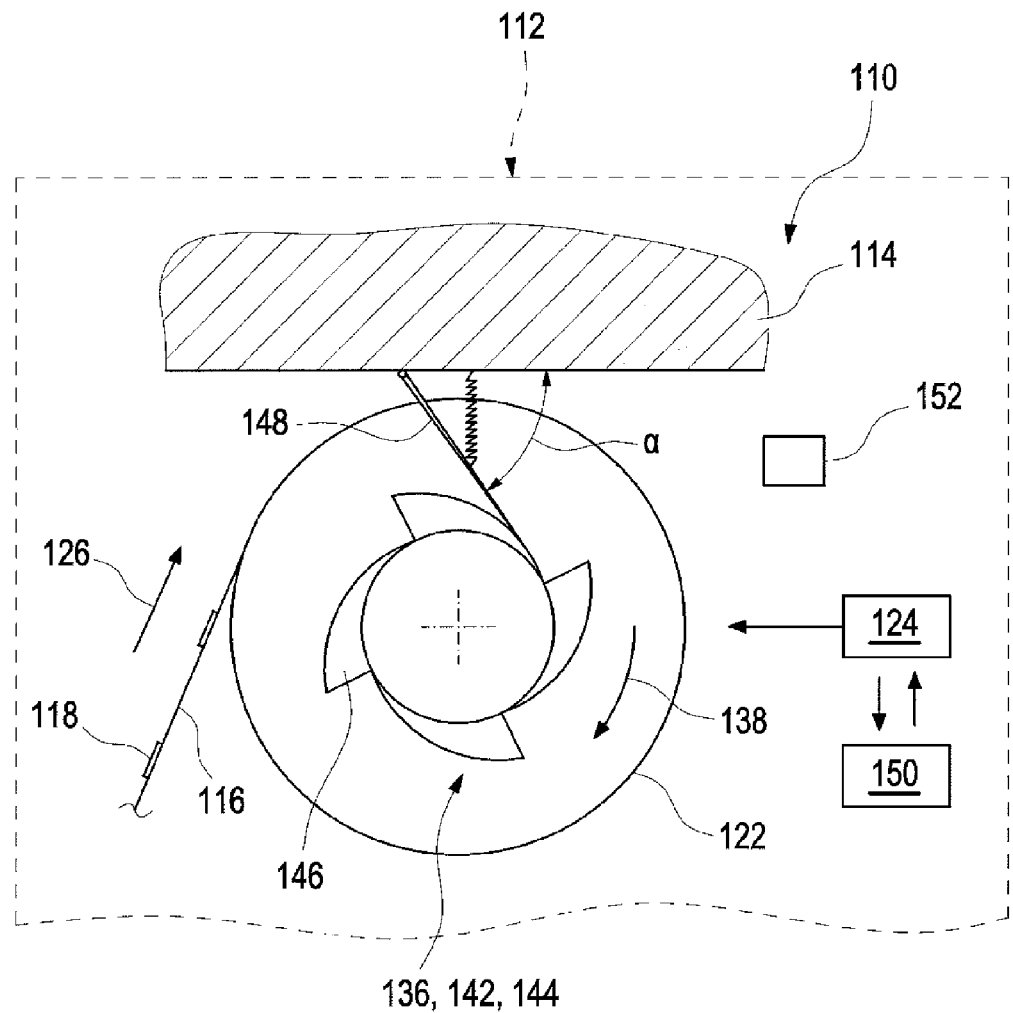
FIG. 1 shows an exemplary embodiment of a tape release device in the form of a rotational-angle-dependent lock, integrated into a rewind lock.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

FIGS. 1 to 6C illustrate different exemplary embodiments of a section of a magazine 110 for use in an analytic test instrument (merely indicated in the figures; reference sign 112). In this exemplary embodiment, the magazine 110 is embodied as a tape magazine and can for example have a magazine housing 114, which is merely indicated in part in the figures. The magazine 110 is embodied as replaceable magazine and can accordingly be replaced.

The magazine 110 has a carrier tape 116 with a plurality of analytic aids 118. By way of example, these analytic aids 118 can be test elements, for example test elements with at least one test field, and/or lancets or microsamplers. An embodiment with different types of analytic aids 118, for example lancets and test elements, is also feasible.

Sections of the carrier tape 116 with still unused analytic aids 118 are wound up on a supply reel 120 (see, for example, FIGS. 5 to 6C; supply reel 120 is not illustrated in the other figures) and sections with already used analytic aids 118 are wound up on a take-up reel 122. By way of example, the analytic test instrument 112 has a drive 124 (merely indicated in the figures), which acts on the take-up reel 122 such that the carrier tape 116 can be spooled through the magazine 110 in a spooling direction 126.

Figure 5:
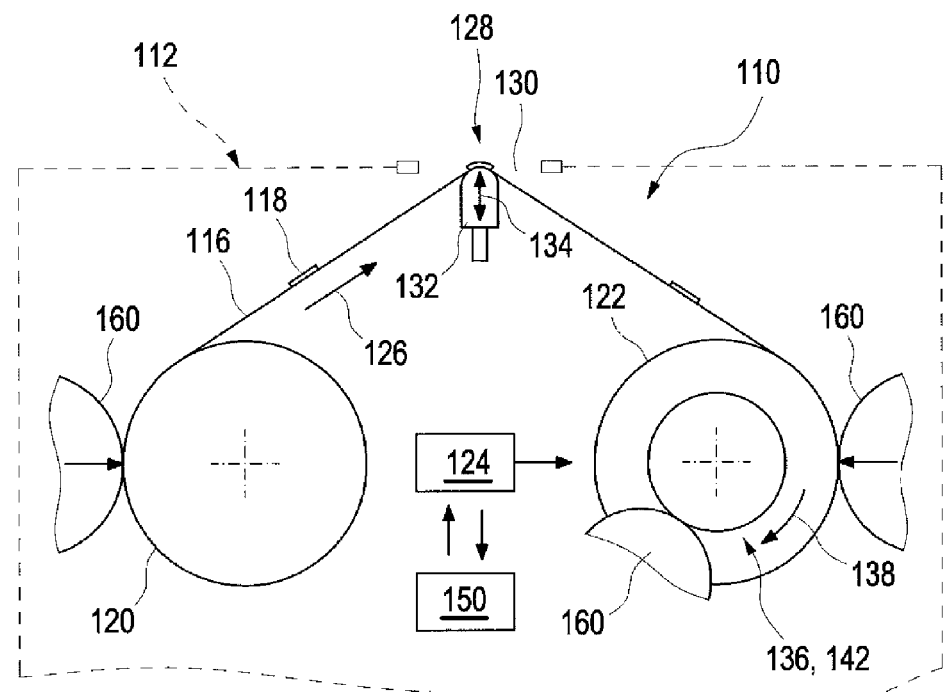
FIG. 5 shows an exemplary embodiment of an optional brake.
Figure 6:
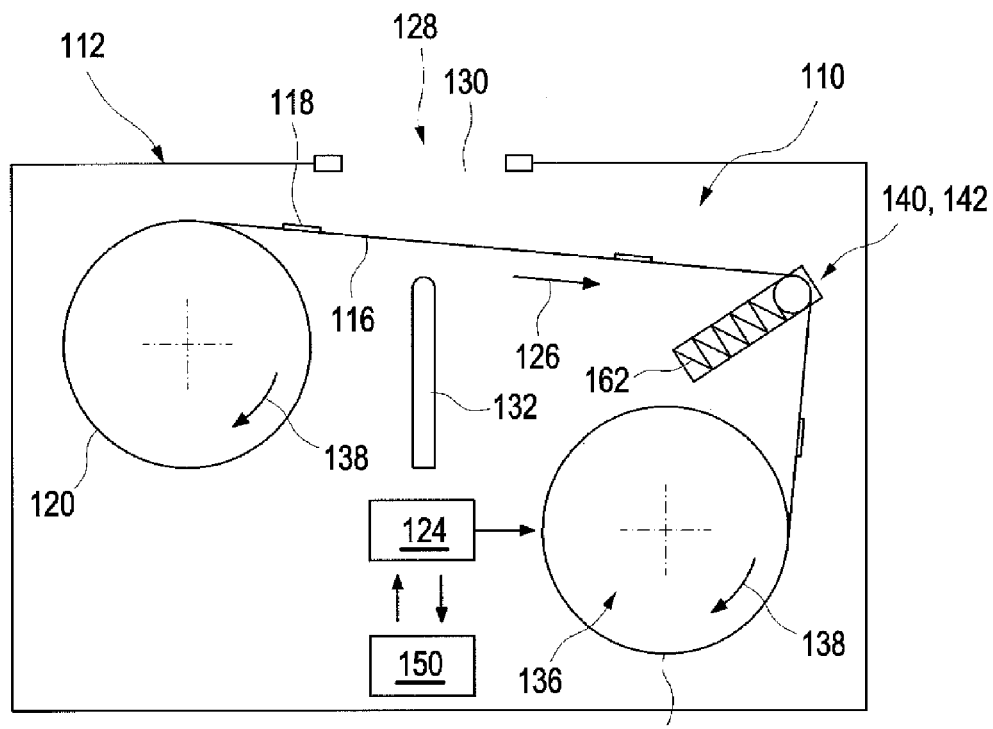
FIGS. 6A to 6C show an exemplary embodiment of a tape release device in the form of a dancer, embodied separately from a rewind lock.
Figure 6:
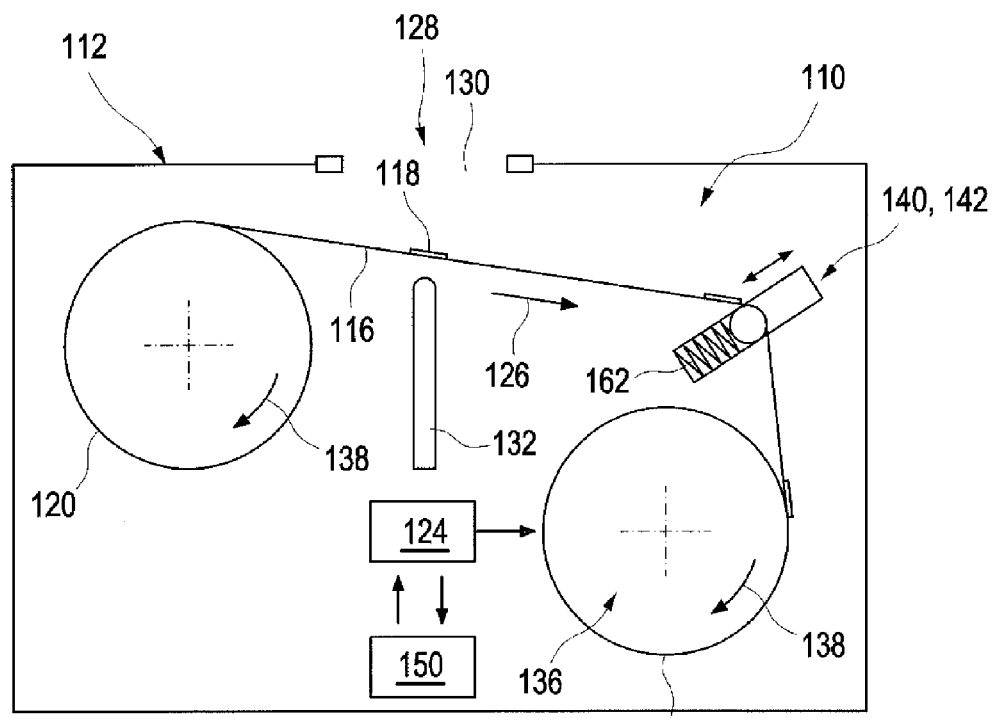
Figure 6:
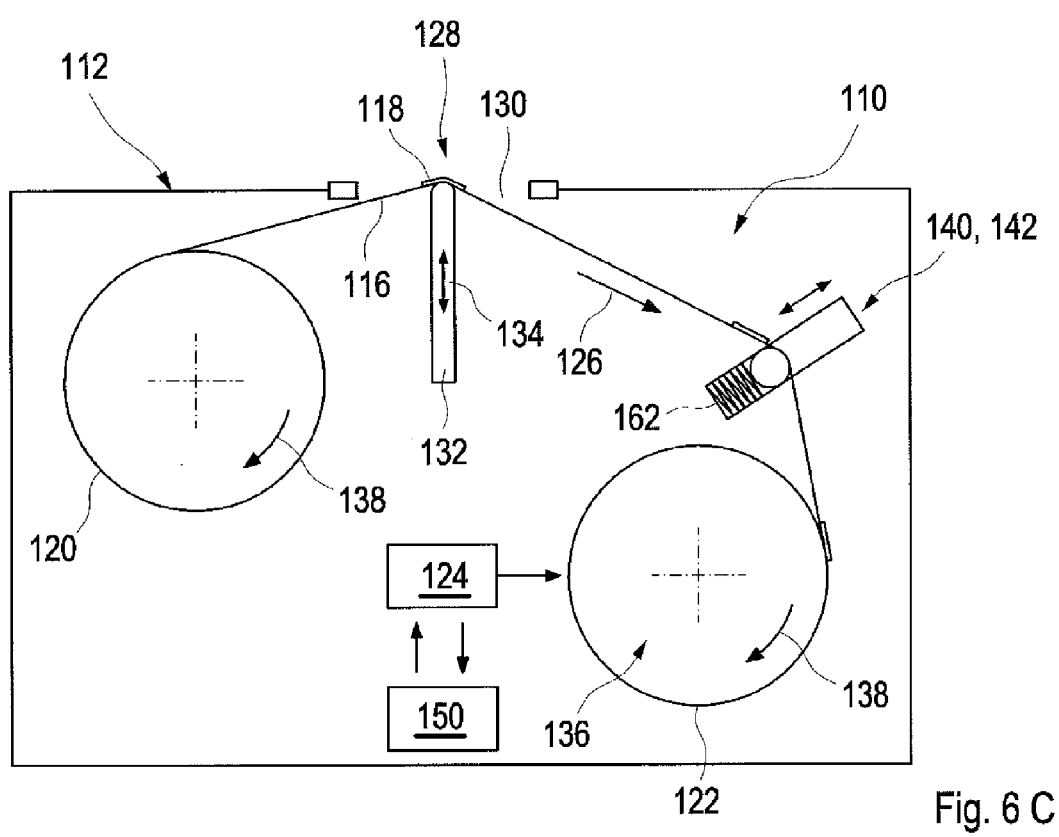

Here, the spooling is cycled such that analytic aids 118 can successively be made available in an application position 128 (indicated in FIGS. 5 to 6C). In this application position 128, a housing of the analytic test instrument 112 and/or the magazine housing 114 can have a perforation 130, through which the analytic aid 118 situated in the application position 128 can interact with a sample outside of the analytic test instrument 112 and/or with skin of a user. If the analytic aid 118 is a lancet, this interaction can, for example, be a lancet movement in the form of a forward movement with piercing of the skin of the user, optionally followed by a return movement. If the lancet is equipped with a capillary, there may, during the return movement, optionally also be a take-up of sample as a result of the capillary effect. If the analytic aid 118 is a test element, for example with at least one test field, the afore-mentioned interaction can be a forward movement during which a sample-taking region of the test element and/or the test field itself is brought into contact with a sample of the body fluid, for example situated on a skin surface of the user, in order to apply the sample onto the test element. The test element can likewise have at least one capillary, for example in order to route the sample from an application point, or a place where the sample is given, to a test field and/or a differently embodied test chemical.

In order to ensure this interaction, the analytic test instrument 112 in the illustrated exemplary embodiments typically has at least one actuator 132. This actuator 132, which is merely indicated in FIGS. 5 and 6A to 6C, is configured to carry out a lifting movement, which, in the figures, is denoted symbolically by reference sign 134 (see FIGS. 5 and 6C). Hence, such a lifting movement 134 is a movement toward a skin surface of the user. The lifting movement 134 in turn can be matched to the type of the analytic aid 118. By way of example, this lifting movement can be a rapid lifting movement with a speed of a few meters per second, provided that the analytic aids 118 comprise a lancet. In this case, the lifting movement is embodied as a piercing movement, optionally accompanied or followed by a sample-taking movement by a capillary during a backward movement of the lifting movement. If the analytic aid 118 comprises a test element, the lifting movement is generally a sample-taking movement, which is typically slow, for example with speeds below 1 meter per second. The actuator 132 can be embodied accordingly, wherein a number of such actuators 132 can also be provided. Thus, the actuator 132 can for example be embodied as a piercing tappet in order to carry out the lancet movement. Alternatively, the actuator 132 can also be embodied as slow sample-taking tappet in order to route e.g. a test element toward a skin surface of the user and back again.

In the illustrated exemplary embodiments, the take-up reel 122 is equipped with a merely indicated rewind lock 136. Hence, this rewind lock 136 is integrated into the magazine 110 and it normally acts at all times, i.e. this rewind lock 136 is not by-passed or weakened when the magazine 110 is inserted into the analytic test instrument 112. In principle, such rewind locks are known from the prior art. By way of example, rotational-direction sensitive elements can be used for this purpose, such as, for example, ratchet wheels, freewheels or the like. These enable a rotation of the take-up reel 122 in a wind-up direction 138 (indicated in FIG. 1), in which the carrier tape 116 moves in the spooling direction 126. By contrast, a rotation of the take-up reel 122 in the opposite direction is prevented, at least to a large extent. However, in contrast to known sample-obtaining systems, provision is made within the scope of these teachings for the at least one rewind lock 136 to be integrated into the magazine 110. This makes it possible to remove the magazine 110 from an instrument, for example a sample-obtaining system, even after at least partial use, with it being possible to reliably prevent there being rewinding and, accordingly, a reuse of already used analytic aids 118 or an undesired unwinding of carrier tape 116.

In the case of such magazines 110 with a rewind lock 136, the above-described problem occurs that there must be a tape release during the lifting movement 134. This tape release takes account of the fact that an additional amount of carrier tape 116 is required in the case of maximum lift of the lifting movement 134; this is also referred to as tape release. For reasons of symmetry, this should be taken in equal amounts from the supply reel 120 and from the take-up reel 122, or from a section of the carrier tape 116 between the application position 128 and the supply reel 120 and the take-up reel 122, respectively. No distinction is made between these options in the following text and the supply reel tape reserve, which comes from the side of the application position 128 facing the supply reel 120, is referred to as tape reserve G and the take-up reel tape reserve, which is taken from the side of the application position 128 facing the take-up reel 122, is referred to as tape reserve S. Then, the following should hold true:

overall tape release=tape reserve S+tape reserve G≈2·tape reserve S.

As already illustrated above, a typical lifting movement 134 at maximum lift lies in the range between 3 and 6 mm. Thus, accordingly, approximately 3 to 6 mm of carrier tape 116 should be provided as tape release such that the take-up reel tape reserve of the take-up reel should typically be between 1.5 and 3 mm. While the supply reel tape reserve of the supply reel can be implemented in a relatively simple fashion since the supply reel 120 is in any case spooled in its release direction when this tape reserve G is released, the situation on the side of the take-up reel is less expedient. The drive 124 of the take-up reel 122 is normally inactive during the lifting movement 134 and thus in many cases blocks a rewinding of the take-up reel 122. Although active rewinding of the drive 124 for the purpose of releasing this tape would be possible, this is comparatively complex from a technical point of view and it is therefore preferably not implemented within the scope of this disclosure. Nevertheless, it is also possible to implement such an active rewinding of the drive 124. Alternatively, or in addition thereto, it would furthermore also be possible to decouple the drive 124 from the take-up reel 122, for example by means of a two-part, spring-mounted take-up reel, which allows at least a small rewind step counter to the wind-up direction 138 under the force influence from the drive of the actuator 132. A third option for implementing a tape release, which can be used as an alternative or in addition thereto, can, as explained in more detail above, comprise a moveably mounted tape deflection, which will be explained below on the basis of FIGS. 6A to 6C and which is also referred to as a "dancer." By way of example, such dancers are known from a tape recorder and can equalize different tensions on the carrier tape 116.

However, these concepts require a tape cassette in which the take-up reel 122 provides the corresponding movement for releasing the take-up reel tape reserve of the take-up reel 122 despite an active rewind lock 136.

To this end, various concepts are proposed, which should be explained in the following text on the basis of FIGS. 1 to 6C. The magazine 110 has a tape release device 142 in all cases. This tape release device 142 is configured to provide the take-up reel tape reserve of the take-up reel 122 (tape reserve S) during the lifting movement 134. In principle, the concepts illustrated in FIGS. 1 to 6C can, in this case, be subdivided into two different groups; however, these groups can also be combined. Thus, FIGS. 1 to 4 show concepts in which the tape release device 142 is integrated into the rewind lock 136 or at least is partly identical with this rewind lock 136 in terms of components. By contrast, FIGS. 6A to 6C show a concept, in which provision is made for a separate tape release device 142, which is designed independently of the rewind lock 136. The tape release device 142 can be only provided on the take-up-reel side, as seen from the application position 128, whereas preferably no such tape release device 142, in particular no moveably mounted tape deflection 140, is provided on the supply-reel side, i.e. in the supply reel 120 and/or on a tape section of the carrier tape 116 between supply reel 120 and application position 128.

In FIG. 1, provision is made for a rotational-angle-dependent lock 144 as a first exemplary embodiment of the tape release device 142. This rotational-angle-dependent lock is a rewind lock 136, which is only effective at specific rotational angles and has slippage therebetween. This slippage must have a sufficient dimension in order to be able to make available the tape reserve S. This is indicated in FIG. 1, with ratchet teeth 146 being provided on the take-up reel 122 in this case. In this case, these ratchet teeth 146 are separated by just about a quarter rotation, and so the slippage in the illustrated exemplary embodiment is no more than 90 degrees. However, other spacings are also possible. The slippage should be dimensioned such that the tape reserve S is less than the distance between adjacent analytic aids 118. This embodiment also holds true for other exemplary embodiments disclosed herein, and so, in general, the tape reserve S is normally less than the distance between adjacent analytic aids 118 in order to prevent the tape release device 142 enabling a previously used analytic aid 118 to once again be spooled back into the application position 128.

By way of example, the ratchet teeth 146 can interact with one or more pawls 148. These can also be spring-mounted, as indicated in FIG. 1. By way of example, the pawl 148 can be associated with a magazine housing 114, and the ratchet teeth 146 with the take-up reel 122. A reverse embodiment is also possible. If the carrier tape 116 is wound up to directly in front of the next active ratchet tooth 146, the slippage until the preceding ratchet tooth 146 blocks can be used for the tape release during the rewind movement of the take-up reel 122 counter to the wind-up direction 138. By way of example, for this purpose, the drive 124 can be rewound and/or the drive 124 can be decoupled from the take-up reel 122 during this time.

In general, the analytic test instrument 112 can for example comprise a control 150 (merely indicated in FIG. 1) in this exemplary embodiment or else in other exemplary embodiments. By way of example, this control 150 can comprise a control logic. By way of example, the control 150 can be coupled to the ratchet function of the tape release device 142. By way of example, provision can be made for at least one sensor 152, which is indicated in FIG. 1 and can also be provided in the remaining exemplary embodiments. By way of example, the signals from this sensor 152 can be routed to the control 150. By way of example, this makes it possible to capture a tilt angle α of the pawl 148, for example of a pawl lever, and use it as e.g. a trigger signal for a delayed stopping function of the drive 124. By way of example, if a ratchet tooth 146 is reached, the drive 124 can be rotated on by a predetermined angle, which may correspond to the tape release S. This angle, through which there is further spooling, may also be configured in a variable manner, for example to take account of different filling degrees of the take-up reel 122 and thus a different conversion of rotational angles into unwound carrier tape 116. As an alternative to detecting an angle of the pawl 148, or in addition thereto, it is also possible to capture a large number of other measurement variables. By way of example, a clicking sound of the ratchet could be used for such a control by means of an acoustic sensor. As another alternative or in addition thereto, use could for example also be made of optical sensors.

In this embodiment, the tape release device 142 is generally only controlled via the rotational angle of the take-up reel 122. As indicated above, this can therefore result in different take-up reel tape reserves as a function of the circumference of the already wound-up tape material of the carrier tape 116. By way of example, this disadvantage can be counteracted by virtue of the slippage being matched to the smallest angle diameter, which corresponds to the state of a still unused magazine 110. Alternatively, as described above, the set slippage in this exemplary embodiment, or else in other exemplary embodiments, can also be matched to the degree of use of the magazine 110 in order to take account of different degrees of being wound-up.

Figure 2:
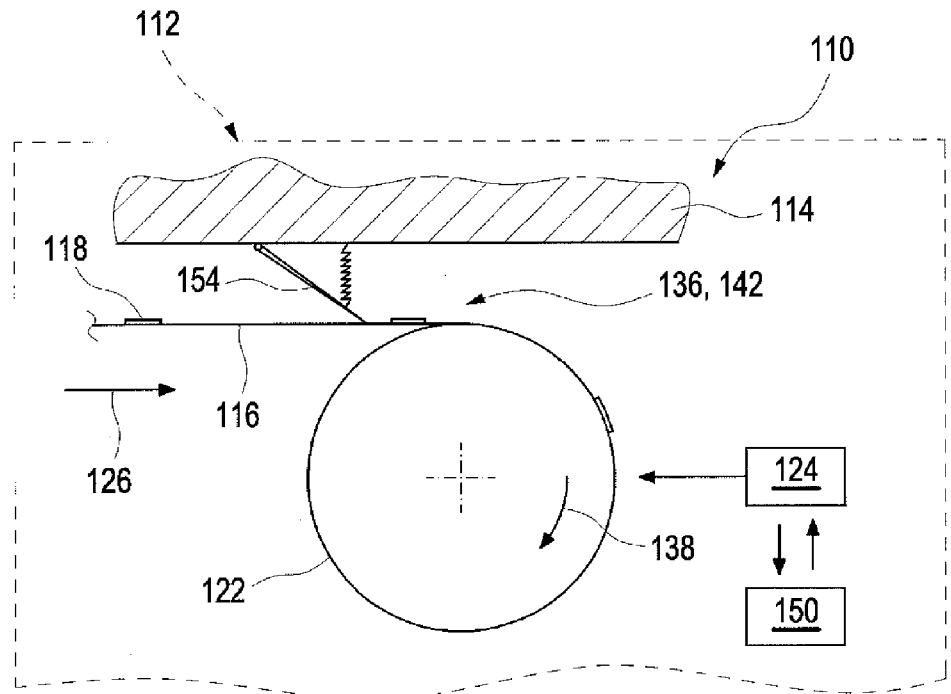
FIG. 2 shows an exemplary embodiment of a tape release device in the form of a spring-loaded flap, integrated into a rewind lock.

FIG. 2 illustrates a second principle of an implementation of a tape release device 142. This exemplary embodiment in turn shows a tape release device 142, which is at least partly integrated into the rewind lock 136. At the same time, this exemplary embodiment shows that the rewind lock 136 need not necessarily be formed on the take-up reel 122. Thus, in place of a rotational-angle-dependent lock 144, FIG. 2 shows that it is also possible to use the fact that the analytic aids 118, for example the lancets, can constitute a mechanical resistance as a result of their thickness. Accordingly, a spring-loaded flap 154 on the input side of the take-up reel 122 is provided in FIG. 2 as a rewind lock 136. Said flap yields in the spooling direction 126 and lets the analytic aid 118 pass. However, in the closed state, the spring-loaded flap 154 lies on the carrier tape 116. In the backward direction, i.e. if the carrier tape 116 moves counter to the spooling direction 126, the flap thus acts as a stop which the analytic aid 118, for example a lancet lying on the carrier tape 116, cannot overcome or which at least constitutes a significant resistance.

The control 150 can in turn be configured to be coupled to a function of the spring-loaded flap 154. By way of example, it is once again possible, although this is not illustrated in FIG. 2, for a sensor 152 to be provided, the latter using the opening of the spring-loaded flap 154 as a trigger signal for a delayed stopping function for the drive 124. After an opening or a renewed closing of the spring-loaded flap 154, it is then only possible to spool on by a predetermined value, which can once again substantially correspond to the tape reserve S.

Figure 3:
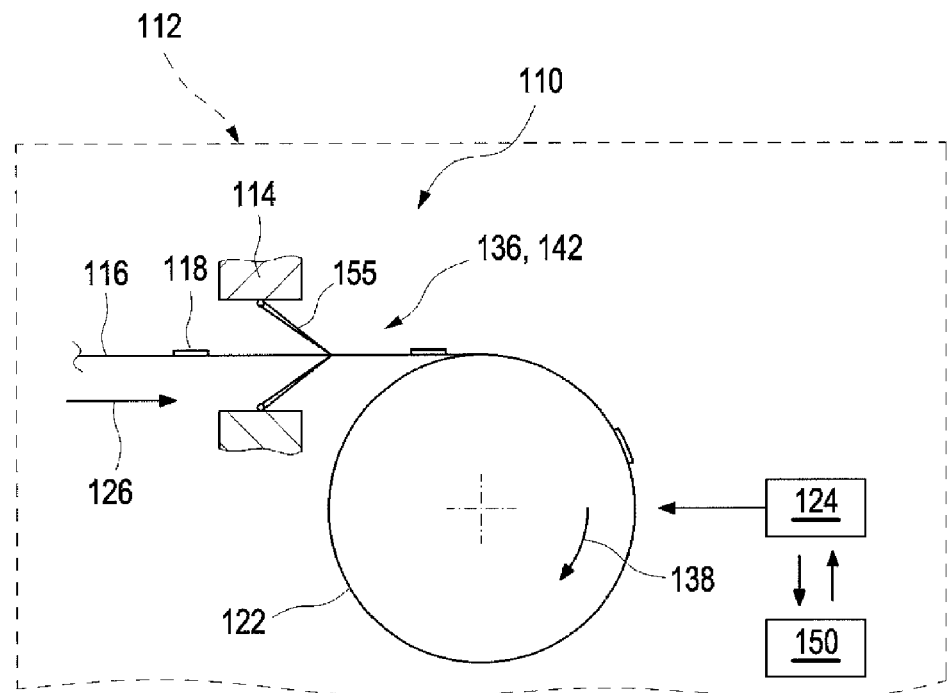
FIG. 3 shows an exemplary embodiment of a tape release device with a sealing lip, integrated into a rewind lock.

The function of the spring-loaded flap 154 in FIG. 2 can also be used by other spring-loaded elements, which also includes elements that are resilient themselves. Thus, FIG. 3 shows an exemplary embodiment that is similar to the exemplary embodiment as per FIG. 2, in which, instead of the spring-loaded flap 154, use is made of a flexible sealing lip 155 on the input side of the take-up reel 122. This sealing lip 155 yields in the spooling direction 126 and lets the analytic aids 118, for example the lancets and/or test elements, pass. However, in the opposite direction, the sealing lip 155 is deformed mechanically plastically and/or elastically and thus increases the friction of the carrier tape 116 within a few millimeters such that the rewinding reel drive 124 is stopped. Hence, the stopping effect can be brought about as a result of two mechanisms, which can also be used in combination. First, there may be a purely mechanical impact of an analytic aid 118 moving in the backward direction on the sealing lip 155, similar to an impact on the spring-loaded flap 154 in FIG. 2. However, as an alternative or in addition thereto, the carrier element 116 itself can also block, for example by, as described above, the sealing lip 155 being moved against its opening direction and deforming, as a result of which friction on the carrier tape 116 is increased.

Figure 4:
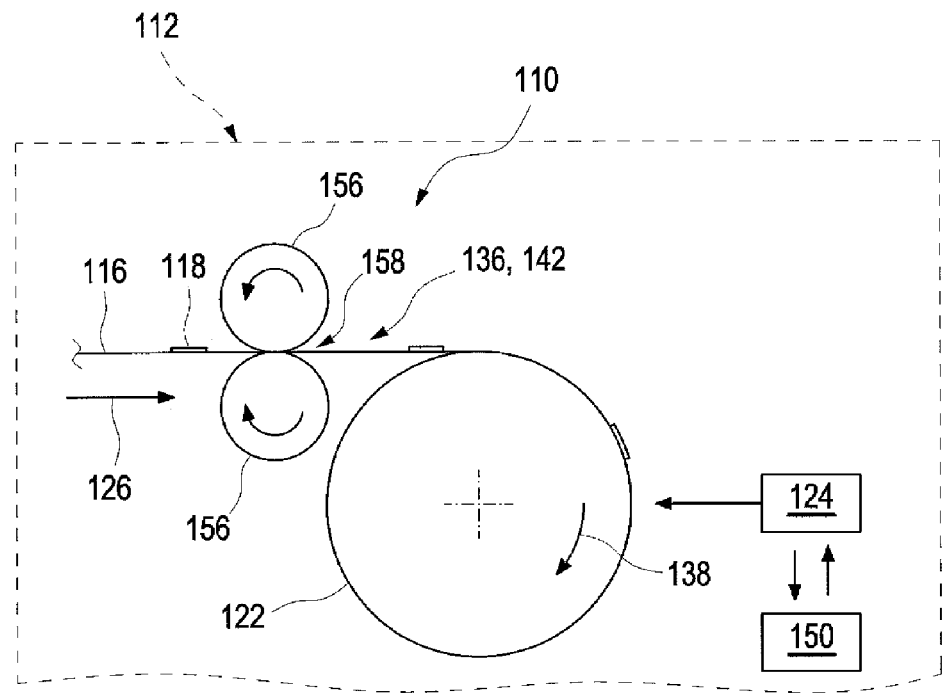
FIG. 4 shows an exemplary embodiment of a tape release device with two rubber rollers, integrated into a rewind lock.

An advantage of the embodiments described in FIGS. 2 and 3, and also of the embodiment in FIG. 4 described below, is that the tape reserve S can be embodied independently of the current reel diameter, i.e. from the degree of being wound onto the take-up reel 122. It is only the actually traveled tape path in FIG. 3 that is decisive for the increase in friction.

As a further alternative exemplary embodiment to FIGS. 1 to 3, FIG. 4 shows a magazine embodied as a cassette with a double rubber roller 156. The carrier tape 116 is routed through a roller gap 158 between the rubber rollers 156. The rubber rollers 156 are embodied such that these only rotate in the spooling direction 126 and block in the opposite direction. The yielding rubber material allows the analytic aids 118, for example the lancets, to pass in the spooling direction 126. However, if the take-up reel 122 is rewound, i.e. if the carrier tape 116 is transported counter to the spooling direction 126, the blocking rubber becomes denser and quickly ensures increasing friction. This stops the reel drive 124 after a few millimeters.

FIG. 5 shows an exemplary embodiment of a magazine 110 and an analytic test instrument 112, which can also be combined with the remaining exemplary embodiments. The magazine 110 in this exemplary embodiment can for example be embodied analogously to the magazines 110 in the exemplary embodiments as per FIGS. 1 to 4. In principle, an embodiment as per the exemplary embodiment in FIG. 6 or as per other exemplary embodiments is also possible. Accordingly, the magazine 110 has at least one rewind lock 136, which is not illustrated in detail in FIG. 5 and which for example can be embodied as per one or more of the embodiments of the rewind lock 136, which are described above and also in the following text. By way of example, the magazine 110 can be embodied as per the magazine illustrated in FIG. 1 and comprise a rewind lock 136 integrated into the take-up reel 122. However, as an alternative or in addition thereto, other embodiments of the rewind lock 136 and/or other components of the magazine 110 are also possible.

In the exemplary embodiment illustrated in FIG. 5, the magazine 110 additionally comprises one or more brakes 160. By way of example, these brakes 160 can act on the carrier tape 116 on the take-up reel 122, on the take-up reel 122 itself or else on the supply reel 120 or the carrier tape 116 on the supply reel 120. A combination of the aforementioned options is also feasible. Thus, the exemplary embodiment comprises a magazine 110, in which the carrier tape 116 is additionally secured by an integrated brake 160. However, the brake 160 can have a wholly or partly separate embodiment from the rewind lock 136, which is not illustrated in detail in FIG. 5. The brake 160 can likewise exert a certain rewind restraint, for example on the take-up reel 122. However, it should be easy to overcome this restraint by applying, preferably a little, force. The brake 160 can thus for example exert a damping property onto the magazine 110 and/or the carrier tape 116 and/or can prevent excessive unwinding of the carrier tape 116.

The brake 160 exerts friction on the carrier tape 116 and/or on one or both of the reels 120, 122. This friction dampens excessive unwinding of tape material. If the brake 160 acts on both reels 120, 122, the reduced friction also exerts this positive damping on both reels 120, 122.

The exemplary embodiments shown in FIGS. 1 to 5 show that a tape release device 142 integrated into the rewind lock 136 can for example be implemented in the form of a ratchet, a rotational-angle-dependent lock, a friction-rotate lock or in the form of an element whose friction on the carrier tape 116 and/or on one or both of the reels 120, 122 depends on a rotational direction and/or a transport direction of the carrier tape 116. By contrast, FIGS. 6A to 6C show an exemplary embodiment in which the tape release device 142 can be implemented independently of the rewind lock 136. As already explained above, this exemplary embodiment is a magazine 110 with a moveably mounted tape deflection 140, which is also referred to as a "dancer" in the following text. In a development of the principle for implementing an instrument-side tape release already described above, it is thus also possible to integrate at least one dancer into the magazine 110, preferably into the cassette. This dancer 140 is preferably only provided on the take-up-reel side of the magazine 110, i.e. on the side of the carrier tape 116 facing the take-up reel 122, as seen from the application position 128. This dancer 140 results in a variable detour of the tape path of the carrier tape 116. Here, a spring force of a spring element 162 is preferably exerted onto the dancer 140. The spring element 162 can also act as return spring. Hence the spring element 162 can always exert a force on the dancer 140 in order to press the latter into its initial position. This initial position is illustrated in FIG. 6A and shows a rest position with a maximum deflection of the dancer 140.

As a result of the transport process of the carrier tape 116, which is illustrated in FIG. 6B, tension is exerted on the carrier tape 116 and on the dancer 140, and this causes the dancer 140 to partly be displaced inward counter to the force of the spring element 162. This is illustrated in FIG. 6B. This is a position of the dancer 140 that can also be referred to as tape transport position and during which the dancer 140 has a medium deflection. As a result of this, the tension on the carrier tape 116 remains constant. At the end of the transport process, the reel motor stops, and a new analytic aid 118 is situated in the application position 128. By way of example, a new lancet can at this stage be gripped by a lancet gripper (not illustrated) of the actuator 132, for example by a new lancet impacting on a stop of the actuator 132 or on the gripper thereof. As a result, the tension remains and the dancer 140 remains in its deflected position.

FIG. 6C finally shows a situation during the lifting movement 134. By way of example, this lifting movement can be a piercing movement or a sample-taking movement. As a result of the deflection of the carrier tape 116, additional tension is exerted on the tape and hence also on the dancer 140 during this lifting movement 134. The dancer 140 is displaced further inward and, in this case, assumes a lift position with a minimum deflection, i.e. a deflection that is not undershot during all the remainder of the process. In the process, the dancer 140 releases the tape reserve S. Here, the spring constant should preferably be configured such that during normal tension, the dancer 140 undergoes a half deflection, at least approximately, i.e., for example, with a deviation of no more than 20%, preferably no more than 10% and particularly preferably no more than 5% from a half deflection.

A great advantage of the embodiment as per FIGS. 6A to 6C consists of the fact that the drive 124, for example the wind motor, need not carry out a rewind movement. Additionally the embodiment solves the problem of loose tape after a lifting movement 134 because the dancer 140 with maximum deflection recaptures this loose tape as a result of the restoring force of its spring element 162.

The analytic test instrument 112 with the magazine 110 as per FIGS. 6A to 6C also has a number of advantages over U.S. Publication No. 2010/0049090, which was already described above. Thus, in particular, it is possible to implement a permanently acting rewind lock 136 in this case, in contrast to known rewind locks that are unlocked when the magazine 110 is inserted into the analytic test instrument 112.

Furthermore, in the exemplary embodiment as per FIGS. 6A to 6C, there is an asymmetric embodiment of the tape release device 142 in the form of the dancer 140. U.S. Publication No. 2010/0049090 discloses the practice of providing moveably mounted tape deflections on both the supply-reel side and the take-up-reel side of the magazine in order to ensure a symmetric deflection of the tape material. However, in practice, under certain circumstances this leads to the dancer 140 being unable to compensate for the additional loose tape from the supply reel after the lifting movement 134. Furthermore, U.S. Publication No. 2010/0049090 teaches an active rewind rotational step of the drive 124 during the piercing movement as an alternative option of the tape release; however, this can result in the problem of the tape being completely loose after the piercing movement. By contrast, in the proposed exemplary embodiment as per FIGS. 6A to 6C, the tape release device 142 may be provided only on the take-up-reel side, whereas no additional tape release device 142 is provided on the supply-reel side, with the exception of the supply reel 120 itself. The dancer 140 solves the problem described above in an elegant manner. Thus it is already partly deflected by the tape transport, as can be identified in FIG. 6B. During the lifting movement 134, for example during the piercing, the carrier tape 116 is generally fixed in the actuator 132, for example in a holder of the gripper. In this manner, both reel sides should be considered independently of one another. On the supply-reel side, the freewheel of the supply reel 120 preferably acts and accordingly releases the tape reserve G. By contrast, on the take-up-reel side the dancer 140 is displaced even further inward and generates the required tape reserve S here. After the piercing or the lifting movement 134 is completed, the carrier tape 116 can be decoupled from the actuator 132, for example from the gripper and/or the holder of the actuator 132, and the dancer 140 can relax completely (see FIG. 6A) and, in the process, again take up the complete tape release.

Hence, overall the exemplary embodiments in FIGS. 1 to 6C show ways of being able to make available a sufficient tape reserve S on the take-up-reel side, despite a rewind lock 136 being present in the magazine 110. In particular, the embodiment variant illustrated in FIGS. 6A to 6C is a particularly advantageous variant since it does not require a rewinding wind drive 124 and hence requires a comparatively uncomplicated embodiment of the analytic test instrument 112. Moreover, this embodiment is able to draw the tape release of the take-up-reel side back in again after the lifting movement 134 and thereby optimize the tape guide. The embodiment with the brake 160 in FIG. 5 is also preferred; however, it can also be combined with the other embodiments since it prevents excessive unwinding of the carrier tape 116, in particular during or after the lifting movement 134.

While exemplary embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

| List of reference signs | |
| --- | --- |
| 110 | Magazine |
| 112 | Analytic test instrument |
| 114 | Magazine housing |
| 116 | Carrier tape |
| 118 | Analytic aid |
| 120 | Supply reel |
| 122 | Take-up reel |
| 124 | Drive |
| 126 | Spooling direction |
| 128 | Application position |
| 130 | Perforation |
| 132 | Actuator |
| 134 | Lifting movement |
| 136 | Rewind lock |
| 138 | Wind-up direction |
| 140 | Moveably mounted tape deflection |

List of reference signs

| | |
|---|---|
| 142 | Tape release device |
| 144 | Rotational-angle-dependent lock |
| 146 | Ratchet teeth |
| 148 | Pawl |
| 150 | Control |
| 152 | Sensor |
| 154 | Spring-loaded flap |
| 155 | Sealing lip |
| 156 | Rubber roller |
| 158 | Roller gap |
| 160 | Brake |
| 162 | Spring element |

What is claimed is:

1. A replaceable magazine for use in an analytic test instrument, comprising:
 a carrier tape having a plurality of analytic aids arranged thereon, wherein the analytic aids can be positioned in an application position of the magazine by the carrier tape;
 a supply reel for holding regions of the carrier tape with unused analytic aids and a take-up reel for holding regions of the carrier tape with used analytic aids, wherein the carrier tape is movable in a spooling direction from the supply reel to the take-up reel;
 the take-up reel comprising a rewind lock, wherein the rewind lock is active during a movement of the analytical aid;
 a tape release configured to make available a tape reserve of the carrier tape on the side of the application position facing the take-up reel, wherein the tape release is only provided on the side of the application position facing the take-up reel, further wherein there is no additional tape release positioned between the supply reel and the application position; and
 a fixing device configured to fix the analytic aids in the application position.

2. The magazine of claim 1, wherein a lifting movement of an analytic aid situated in the application position has a maximum lift distance of 2 mm to 10 mm, further wherein the take-up reel tape reserve is 0.2 to 0.8 of the maximum lift.

3. The magazine of claim 1, wherein the magazine is configured to make available a supply reel tape reserve of the carrier tape on the side of the application position facing the supply reel, wherein the supply reel tape reserve substantially corresponds to the take-up reel tape reserve.

4. The magazine of claim 1, wherein the tape release is configured to hold the take-up reel tape reserve after the lifting movement of the analytic aid.

5. The magazine of claim 1, wherein the rewind lock is a permanent rewind lock.

6. The magazine of claim 1, wherein the rewind lock comprises at least one of the following: a rotational-direction sensitive element connected to the take-up reel, wherein the rotational-direction sensitive element enables a rotation in one direction and at least largely prevents a rotation in another direction; a freewheel connected to the take-up reel; a ratchet connected to the take-up reel; a pawl connected to the take-up reel; a rotational-direction-dependent brake acting on the carrier tape; a spring-loaded element acting on the carrier tape; a spring-loaded flap acting on the carrier tape; a sealing lip acting on the carrier tape.

7. The magazine of claim 1, further comprising at least one brake, wherein the brake is configured to brake rewinding of the take-up reel and/or winding-on of the supply reel.

8. The magazine of claim 1, wherein the tape release is at least partly integrated into the rewind lock.

9. The magazine of claim 1, wherein the rewind lock comprises a plurality of spaced locking positions, wherein a movement of the carrier tape counter to the spooling direction is possible between adjacent locking positions, whereby the take-up reel tape reserve is at least partly released when the carrier tape moves counter to the spooling direction.

10. The magazine of claim 1, wherein the rewind lock has a rotational-direction sensitive element connected to the take-up reel, the rotational-direction sensitive element enabling a rotation in one direction and at least largely preventing a rotation in another direction, wherein the rotational-direction sensitive element has a dead angle and enables rewinding through the dead angle to release the take-up reel tape reserve.

11. The magazine of claim 1, wherein the rewind lock comprises a spring-loaded element acting on the carrier tape, wherein the analytic aids can pass the spring-loaded element when the carrier tape moves in the spooling direction, wherein the analytic aids and/or the carrier tape jam against the spring-loaded element when the carrier tape moves counter to the spooling direction.

12. The magazine of claim 11, wherein the spring loaded element comprises a spring-loaded flap and/or a sealing lip.

13. The magazine of claim 1, wherein the rewind lock has a roller and the carrier tape is routed through a gap delimited by the roller, wherein the roller undergoes a deformation when the carrier tape moves counter to the spooling direction and the deformation leads to a narrowing of the gap whereby further movement of the carrier tape is impeded.

14. The magazine of claim 1, wherein the tape release operates at least partly independently of the rewind lock.

15. The magazine of claim 14, wherein a moveably mounted tape deflection is provided between the application position and the take-up reel.

16. An analytic test instrument, comprising:
 a magazine as claimed in claim 1, the magazine being replaceably receivable in the analytic test instrument; and
 a drive for driving the carrier tape of the magazine, the analytic test instrument being configured to carry out a lifting movement of an analytic aid situated in the application position.

17. The analytic aid of claim 16, wherein the lifting movement comprises a piercing movement and/or a sample-taking movement.

18. The analytic test instrument of claim 17, further comprising a sensor for identifying the position of the carrier tape and a control configured to set the take-up reel tape reserve in accordance with the identified position of the carrier tape.

19. The analytic test instrument of claim 18, wherein the rewind lock comprises a plurality of locking positions, the take-up reel tape reserve being released when the carrier tape moves counter to the spooling direction between two of the locking positions, further wherein the control enables onward transport of the carrier tape equal to the take-up reel tape reserve when a predetermined locking position is reached.

20. The magazine of claim 1, wherein the fixing device comprises a gripper configured to fix the analytic aids in the application position.

* * * * *